(12) United States Patent
Grane

(10) Patent No.: US 8,932,267 B2
(45) Date of Patent: Jan. 13, 2015

(54) INFLATABLE FACE SEAL FOR A RESPIRATORY MASK AND METHOD OF PRODUCING SAME

(75) Inventor: Christian Grane, Kokkedal (DK)

(73) Assignee: AMBU A/S, Ballerup (DK)

( * ) Notice: Subject to any disclaimer, the term of this patent is extended or adjusted under 35 U.S.C. 154(b) by 1499 days.

(21) Appl. No.: 12/521,988

(22) PCT Filed: Jan. 2, 2007

(86) PCT No.: PCT/DK2007/000001
§ 371 (c)(1),
(2), (4) Date: Jan. 8, 2010

(87) PCT Pub. No.: WO2008/080396
PCT Pub. Date: Jul. 10, 2008

(65) Prior Publication Data
US 2010/0170516 A1    Jul. 8, 2010

(51) Int. Cl.
*A61M 5/00* (2006.01)
*A61G 10/00* (2006.01)
*A62B 7/10* (2006.01)
*A62B 23/02* (2006.01)

(52) U.S. Cl.
USPC .............. 604/207; 128/202.12; 128/205.28

(58) Field of Classification Search
USPC ............ 128/202.28, 205.12, 205.13, 205.17, 128/205.25
See application file for complete search history.

(56) References Cited

U.S. PATENT DOCUMENTS

| | | | |
|---|---|---|---|
| 3,330,274 A | | 7/1967 | Bennett |
| 4,062,357 A | * | 12/1977 | Laerdal ................. 128/206.26 |
| 4,770,169 A | * | 9/1988 | Schmoegner et al. ... 128/207.13 |
| 4,873,972 A | * | 10/1989 | Magidson et al. ....... 128/206.12 |
| 6,494,206 B1 | * | 12/2002 | Bergamaschi et al. .. 128/206.24 |
| 7,243,650 B2 | * | 7/2007 | Thornton ................ 128/205.25 |

FOREIGN PATENT DOCUMENTS

| | | |
|---|---|---|
| EP | 0 602 424 A1 | 6/1994 |
| WO | WO-97/07847 | 3/1997 |
| WO | WO-2007/059504 A2 | 5/2007 |

* cited by examiner

*Primary Examiner* — Nicholas Lucchesi
*Assistant Examiner* — Ian Holloway
(74) *Attorney, Agent, or Firm* — Finnegan Henderson Farabow Garrett & Dunner LLP

(57) ABSTRACT

An inflatable face seal (1'; 30') for a respiratory mask, the inflatable face seal comprising an annular air-tight hollow portion (12'; 40') where a cross section through one section of the annular hollow portion (12; 40) comprises a bonded joint (11; 41) which joins two overlapping flanges (6,7; 35,36). The two flanges are bonded together such that an inwardly facing surface (10; 39) of a first flange (6; 35) of the two overlapping flanges is in contact with an outwardly facing surface (9; 38) of a second flange (7; 36) of the two overlapping flanges. In this way, the bond is strong and only exposed to shear stresses when the annular air-tight hollow portion is exposed to increased pressure.

9 Claims, 5 Drawing Sheets

INFLATABLE FACE SEAL FOR A RESPIRATORY MASK AND METHOD OF PRODUCING SAME

This application is a 371 of PCT/DK2007/000001, filed Jan. 2, 2007.

BACKGROUND OF THE INVENTION

The invention relates to an inflatable face seal for a respiratory mask such as, for example, an anaesthesia face mask and/or a respiratory face mask. Such face masks are typically used during the medical treatment of patients. The inflatable face seal comprises an annular air-tight hollow portion where a cross section through one section of the annular hollow portion comprises a bonded joint which joins two overlapping flanges.

In typical applications, the inflatable seal of the current invention is used in face masks which consist of a relative stiff shell portion, and an inflatable annular face seal attached to the circumference of the shell via an air tight connection. Such a mask is disclosed in EP 0 602 424. However, the face seal of the current invention could also be used for face masks which consist of a single injection moulded element comprising both a semi rigid shell portion and an inflatable annular face seal in accordance with the current invention.

Such inflatable annular face seals are currently produced in a variety of designs to provide different levels of anatomical fit, ease of use, durability, and ease of cleaning and sterilizing. In addition, during the production of such face seals, it is desired to maintain a low cost of manufacturing.

However the prior art masks can be difficult to manufacture. In particular, since the final mask comprises an annular hollow and air-tight internal portion, the mask cannot be directly formed by an injection moulding or rubber dipping procedure. The masks are therefore usually formed in a two part process where the masks are first moulded using an annular internal core used to form the hollow internal portion. Once the mask is moulded, the mask is stripped from the core via an opening in the mask, the opening being arranged along the circumference of the annular hollow portion. Once the core is removed, then the opening is closed and sealed to form an airtight bonded joint.

The bonded joint is usually made by an adhesive placed between two flanges of the mask. However, since the curing time of the adhesive is usually around one day, a fixture is required to press the two flanges together in order to ensure that the bond is effective. This procedure requires a very large number of fixtures. For example, if the production capacity of the manufacturing operation is 500 masks a day, then at least 500 fixtures are required during the curing process. Acquisition and management of all the fixtures makes the production costs rather expensive and the production process complex.

Furthermore, as EP 0 602 424 shows, the two surfaces which are bonded together are usually arranged as two parallel flanges where the bond is formed between two "inwardly facing" surfaces of the flanges. By inwardly facing is meant surfaces which face in towards the centre of a cross section of a portion of the annular hollow portion. In this way, when pressure is applied to the inner volume of the mask, for example during machine washing and sterilization, the bond is exposed to "peel" forces which attempt to peel the bonded surfaces away from each other. "Peel" forces are hard on the bond since the stresses are applied to the limited area at the inside edge of the bonded joint.

One aspect of the current invention is therefore to provide a design of an inflatable annular face seal which allows the seal to be manufactured at low cost in a variety of elastomeric materials suitable for single use products or reusable products.

Another aspect of the current invention is to provide an inflatable face seal as mentioned in the introductory paragraph which has high durability to repeated use and exposure to cleaning and sterilization procedures.

SUMMARY OF THE INVENTION

The above mentioned aspects are in part solved by an inflatable face seal as mentioned in the opening paragraph where the two flanges are bonded together such that an inwardly facing surface of a first flange of the two overlapping flanges is in contact with an outwardly facing surface of a second flange of the two overlapping flanges.

It should be noted that in the current specification, an "inwardly facing surface" is meant to indicate a surface which faces in towards the interior of the hollow portion whereas an "outwardly facing surface" is meant to indicate a surface which faces outwards and away from the interior of the hollow portion.

In one embodiment, internal stresses in the inflatable face seal can force the inwardly facing surface of the first flange towards the outwardly facing surface of the second flange. In this way, the internal stresses hold the flanges together without the need for any external forms during the curing of the bond. The internal stresses could be generated at the time when the bonded joint is made. The internal stresses could for example be generated by stretching a portion of the walls of the inflatable face seal and then holding the walls in a stretched position.

The cross section of the hollow portion could furthermore comprise an enclosed area and the bonded joint could be located on the periphery of said enclosed area. This arrangement provides a simple geometric form and results in a strong bond. In a preferred embodiment, the two flanges can be arranged parallel to each other.

The second flange could also be formed as a flange which protrudes from an outer wall of the inflatable face seal and the first flange could be formed as a hook attached to an inner wall of the inflatable face seal. This provides for an arrangement where the first flange can be "hooked" around the second flange.

The flanges can also be arranged such that the first flange extends along the periphery of the cross section of the annular hollow portion in an opposite direction as the second flange. In this way, a bonded joint is provided which results in shear stresses being applied to the bond between the two flanges when pressure is applied to the hollow portion instead of peal forces.

A preferred method of manufacturing an inflatable face seal for a respiratory mask comprises the steps of: moulding an inflatable face seal having an annular hollow portion where a cross section through one portion of the annular hollow portion has a first flange and a second flange which are overlapping and radially spaced apart such that the first flange is arranged underneath the second flange in the radial direction, applying an adhesive to an outer surface of the second flange, and stretching a portion of said cross section located between the first flange and the second flange in order to fold the first flange over the second flange, such that an inner surface of the first flange is in contact with said outer surface of the second flange and such that the first flange is forced against the second flange via the internal stresses in the moulded part due to the stretching.

It should be mentioned that "radially" in this specification should be interpreted as being in a direction along a radius. It should however be noted that the term radius does not limit the invention to circular shapes. The cross section of the annular hollow portion can be any shape. However, the general shape of the cross section is a shape which surrounds an area. This area has a centre and the "radius" in this case is defined as the vector from the centre out to a point on the cross section. The radius is not constant along the cross section, but could be of varying length. It should also be noted that the cross section is open when the seal is removed from the mould and the area is not completely enclosed by the cross section.

In a preferred method, the inflatable face seal can be moulded via an injection moulding process in a closed mould. By using a closed mould, it is possible to vary the wall thickness of the moulded part.

An intermediate product in the manufacturing process of an inflatable face seal for a respiratory mask comprises an annular cavity which has a cross section comprising an open semi circular portion having a first flange and a second flange arranged on opposite ends of the open semi circular portion. The second flange can be arranged such that it overlaps the first flange and can be arranged farther from the centre of the open semi circular portion than the first flange. The first flange could furthermore extend in an opposite direction than the second flange.

In one embodiment of the intermediate product, the first flange and the second flange could be arranged essentially parallel to each other.

It should be noted that the term "open semi circular portion" should be understood for the purpose of this specification as a portion which does not have to be circular, but could be any geometric shape. However, in general, the portion encloses a defined area. The portion is however "open", meaning that the walls of the portion at some point define an opening.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

In the following, the invention will be described in greater detail with reference to the embodiments shown by the enclosed figures. It should be emphasized that the embodiments shown are used for example purposes only and should not be used to limit the scope of the invention.

Please note that all references to orientations in this specification, for example horizontal, vertical, upper, lower, top, bottom, etc. shall be understood with reference to the orientations shown in the figures.

DETAILED DESCRIPTION

Figure 1:
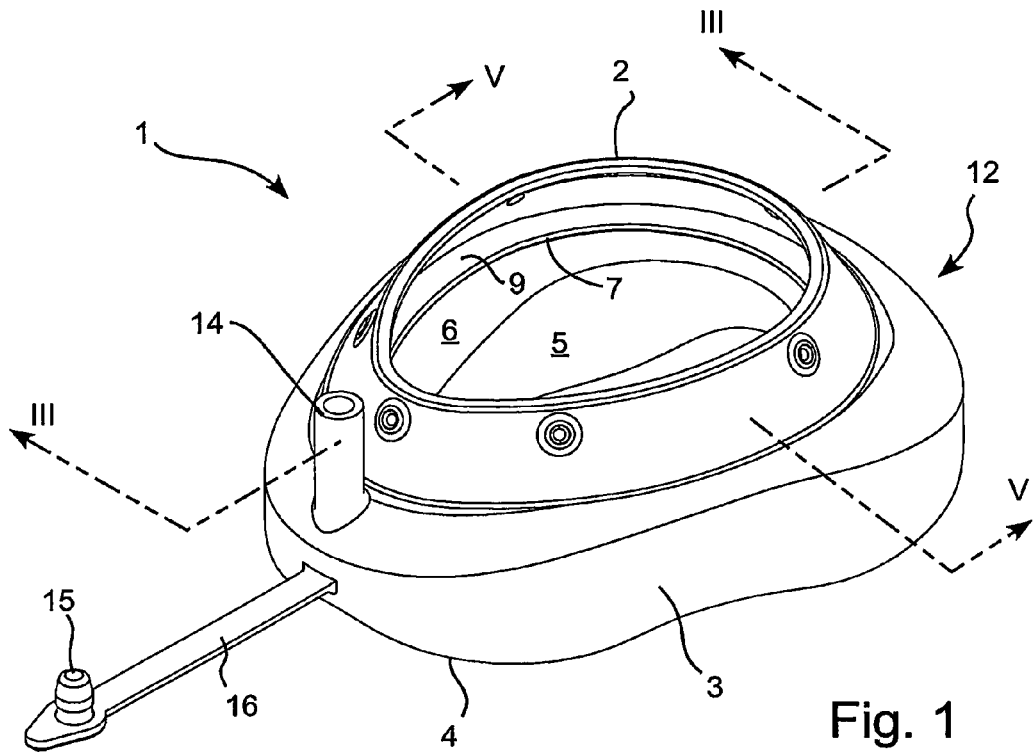
FIG. 1 shows a perspective view of a first embodiment of an inflatable face seal according to the invention before gluing.
Figure 2:
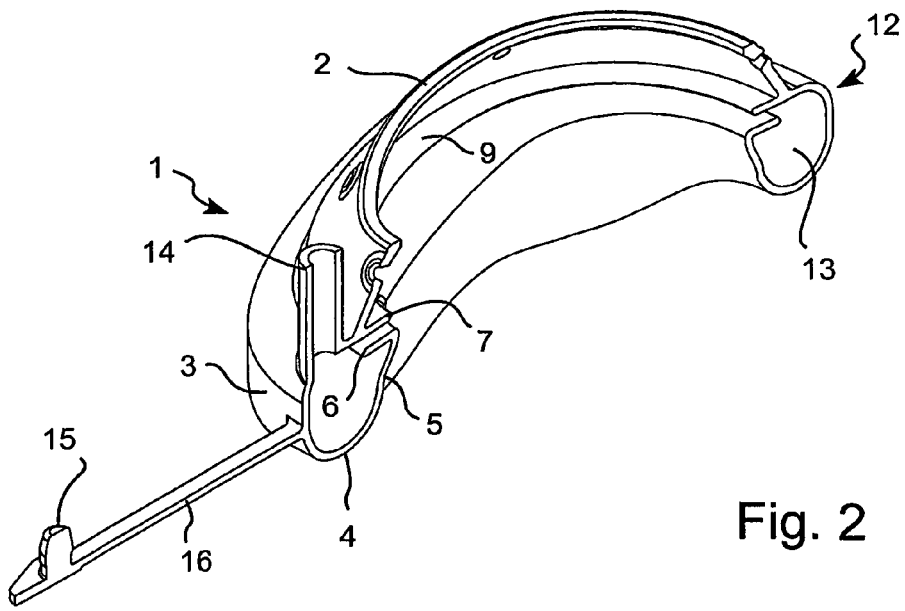
FIG. 2 shows a perspective cross section view of the inflatable face seal shown in FIG. 1.
Figure 3:
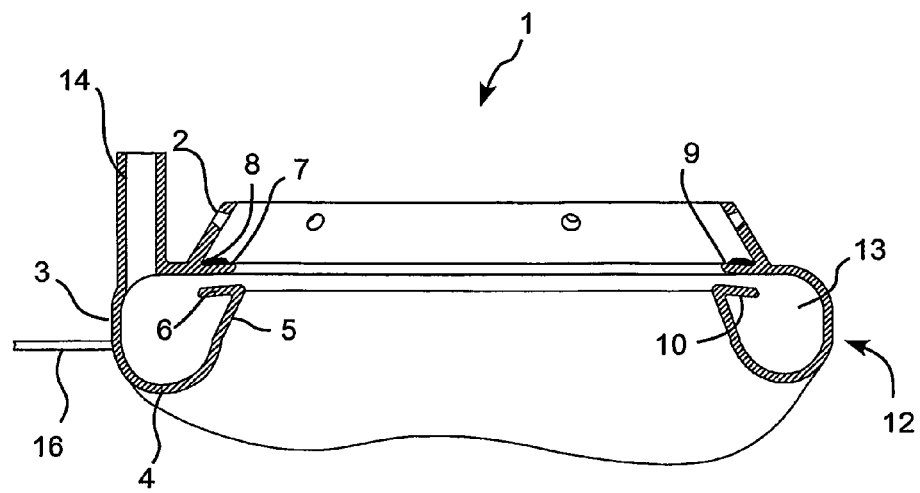
FIG. 3 shows a cross section view of the inflatable face seal shown in FIG. 1 according to the line III-III.
Figure 4:
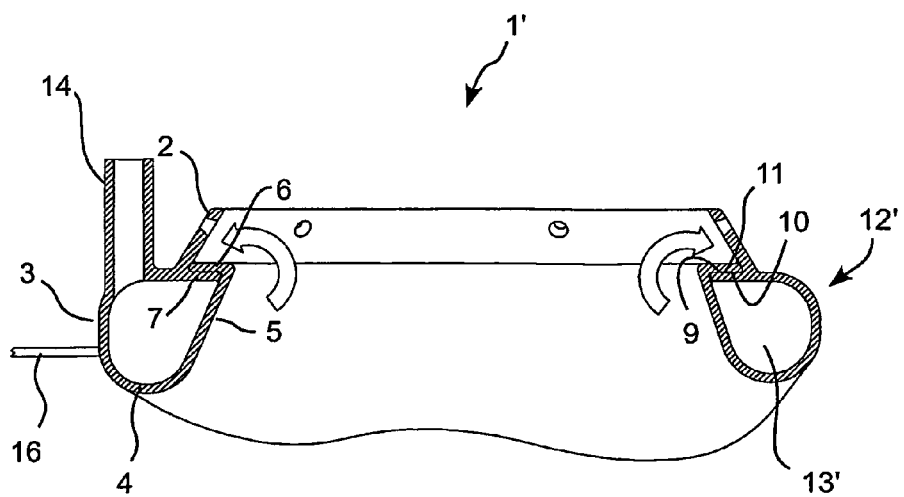
FIG. 4 shows a cross section view of FIG. 3 after gluing.
Figure 5:
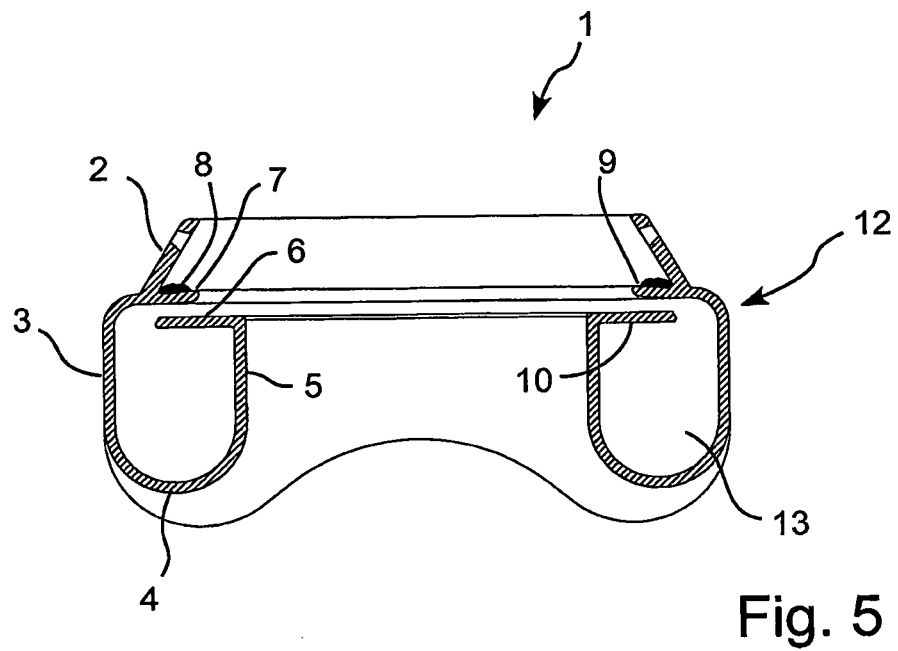
FIG. 5 shows a cross section view of the inflatable face seal shown in FIG. 1 according to the line V-V.
Figure 6:
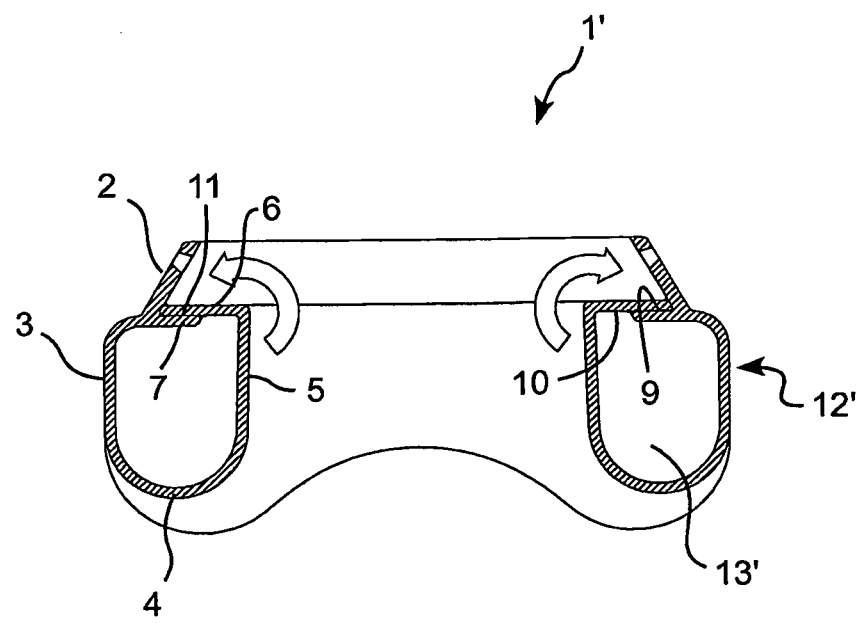
FIG. 6 shows the cross section view of FIG. 5 after gluing.

According to the present invention a preferred embodiment 1 is shown in FIGS. 1-6. FIGS. 1, 2, 3 and 5 show the shape of the single injection moulded part 1 as formed in the mould. This could be called an "intermediate product" 1 which is present during the manufacturing process of the inflatable face seal. FIGS. 4 and 6 show the shape of the part 1' after gluing. This could be called the final part 1' after the manufacturing process is complete.

The inflatable face seal 1 comprises an attachment sleeve 2 which allows for annular attachment to the circumference of the rigid mask shell (not shown). The inflatable face seal further comprises an outer wall 3, a curved wall 4, an inner wall 5, a first flange 6 and a second flange 7. The outer wall 3 extends outwards and down from sleeve 2. The curved wall 4 is a continuation of the outer wall 3 and forms an anatomical shape which abuts the face of the user (not shown) during use. The inner wall 5 connects to the curved wall 4 and is a continuation thereof. The first flange 6 is attached at the end of the inner wall 5 and is recessed at a distance below the level where sleeve 2 meets the outer wall 3. The second flange 7 extends inwards from the attachment sleeve 2, in parallel and overlapping the first flange 6 with a small gap between them.

After injection moulding, an adhesive 8 such as glue is applied to the upper or outwardly facing surface 9 of the second flange 7. The inner wall 5 is then stretched outwardly and upwardly to allow the first flange 6 to be folded over the second flange 7 and to be seated on top of the adhesive, where an inner surface 10 of the first flange will be slightly pressed against the adhesive by the elastic forces created by the axial displacement. The inflatable face seal may therefore be left to cure without any need for fixtures during curing, as shown in FIGS. 4 and 6. In this way, the adhesive forms a bonded joint 11 between the two flanges. The final product 1' as shown in FIGS. 4 and 6 therefore comprises an annular air-tight hollow portion 12'. FIGS. 4 and 6 also show that a cross section through one portion of the annular air-tight hollow portion defines an enclosed area 13' and that the bonded joint 11 lies on the periphery of this enclosed area.

In addition to the ease of manufacturing and the freedom to select between a wide range of materials, the design also has the additional advantage that the adhesive bond is only exposed to shear forces when the pressure is increased inside the inflated seal. This ensures a much more durable bonding than adhesive bonding on previous face mask seals which are exposed to peeling when the pressure inside the seal is increased.

The inflatable face seal 1 further comprises an inflation tube 14 which is moulded as an integral part of the face seal. In addition, a closing stopper 15 is attached by a strap 16 to the outer wall. However, in certain cases, an inflation tube is not necessary, for example in disposable masks. The main reason for the inflation tube is to prevent excessive pressure from building up in the annular hollow portion 12' during washing/sterilization by providing an opening for the air-tight hollow portion 12'.

As can be seen from FIGS. 3-6, the first flange 6 is formed as a sort of hook which hooks around the second flange 7 in the assembled state of the inflatable face seal. However, the function of the hook is to hold the flanges together when the first flange is stretched and folded around the second flange. It is possible to form the two flanges in many different ways to achieve the same function. For example, instead of forming the two flanges as a hook and a protruding flange, the two flanges could be formed as two correspondingly curved flanges which engage with each other in the assembled state of the inflatable face seal and prevent relative displacement between the flanges while the glue cures.

It can also be noted from FIGS. 3-6 that the flanges are formed in such a way that they extend in opposite directions. By opposite directions is meant along the circumference or periphery of the cross section of the annular hollow portion. In this way, the two flanges extend towards each other and overlap each other. When the two flanges are bonded together in this way, stresses in the walls of the annular hollow portion 12' due to pressure inside the annular hollow portion will apply a shear stress to the bond instead a stress which pulls the surfaces away from each other as is the case in the prior art.

It should be noted that the embodiment shown in the figures is meant to be used in a two part mask comprising the seal part and a rigid mask part. However, the invention could also be applied to masks which are moulded as one single piece comprising both a seal part and a mask part.

Furthermore, it should be noted that the embodiment shown has an integrated attachment sleeve 2 for connecting the inflatable face seal 1 to a rigid mask part. However, it could be imagined that the attachment sleeve was a separate part which was attached to the inflatable face seal via gluing.

Figure 7:
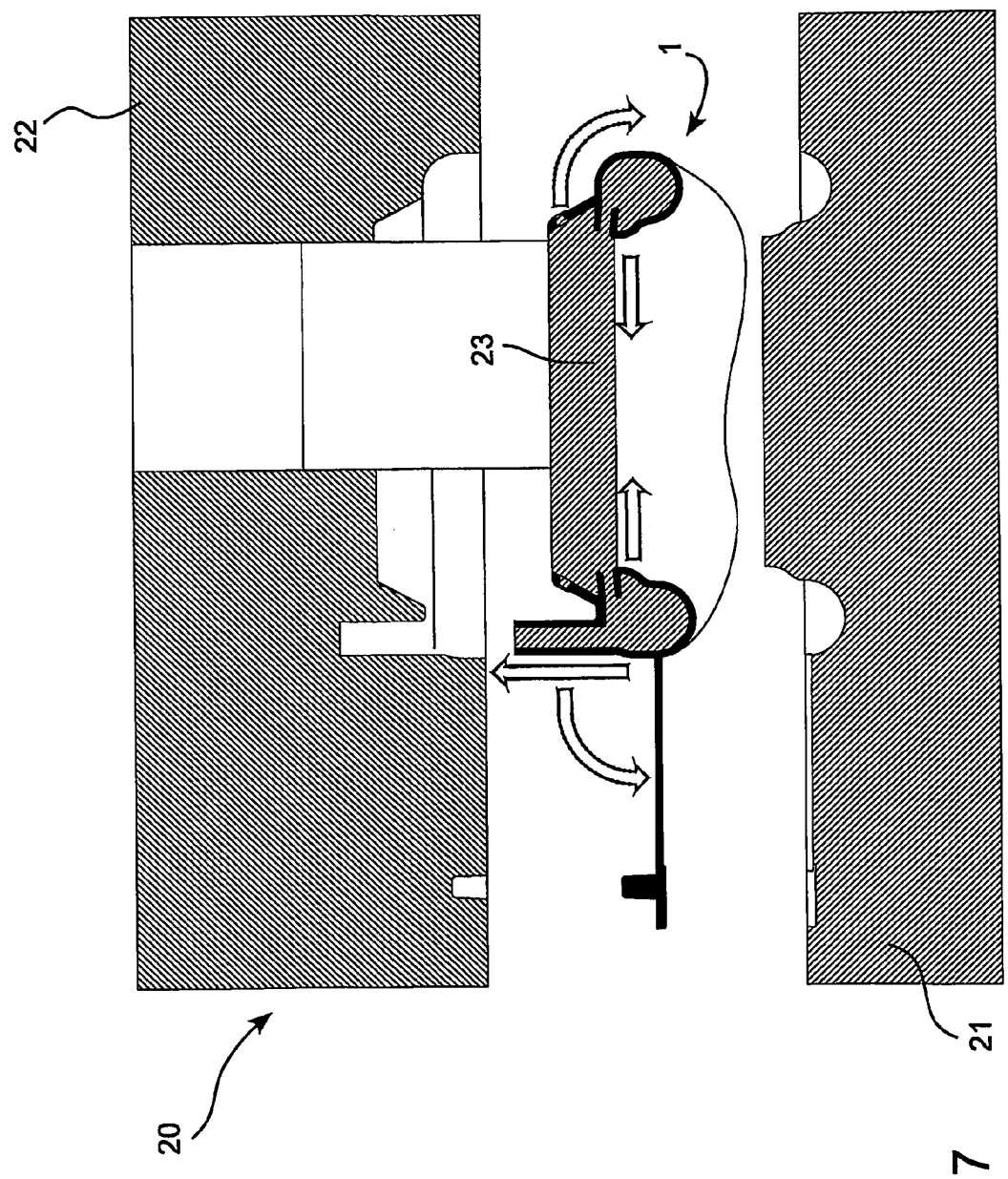
FIG. 7 shows a cross section view of an example of one embodiment of a mould for injection moulding the inflatable face seal shown in FIG. 1.

FIG. 7 shows an example of a mould 20 used in the injection moulding of the inflatable face seal 1 shown in FIGS. 1-6. The mould is comprised of three parts, a bottom part 21, a top part 22 and an internal annular core 23. The top part 22 and the internal annular core 23 are arranged vertically displaceable with respect to the bottom part 21. When the mould is closed, the internal annular core is suspended between the top part and the bottom part. The material of the face seal is then injected into the mould. Once the material has hardened, the top part 22 and the internal core 23 are moved upwards. The face seal remains attached to the internal core 23. The face seal can then be peeled off the internal core 23.

It should be noted that due to the arrangement of the mould, which is a closed form, it is possible to vary the thickness of the wall thickness of the injection moulded part. This can be used for example to make the inner 5, outer 3 and curved 4 walls thin and the two flanges 6,7 thicker. This increases the flexibility of the walls while maintaining the strength of the flanges.

Figure 8:
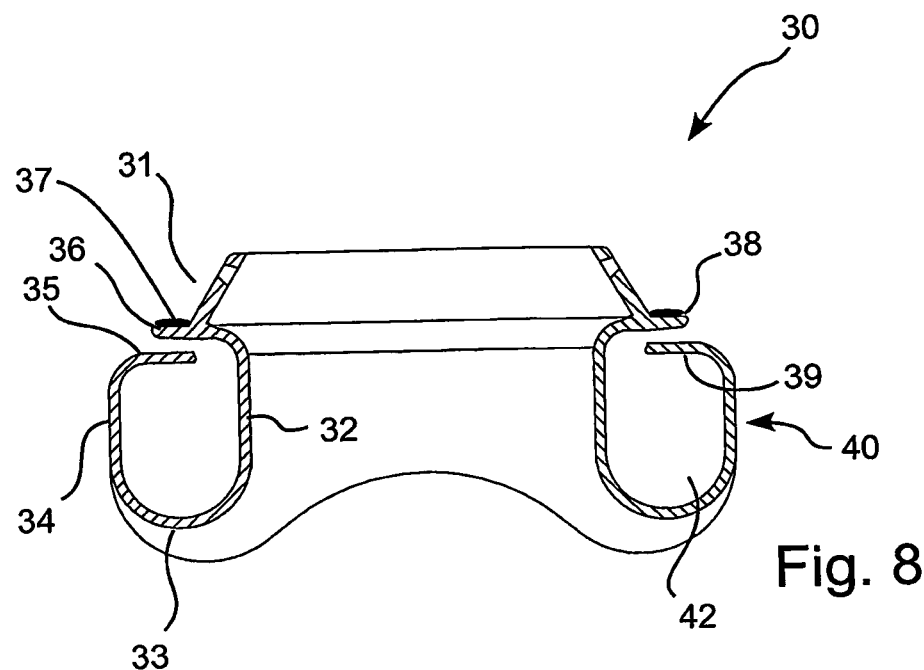
FIG. 8 shows a cross section view of a second embodiment of an inflatable face seal prior to gluing.
Figure 9:
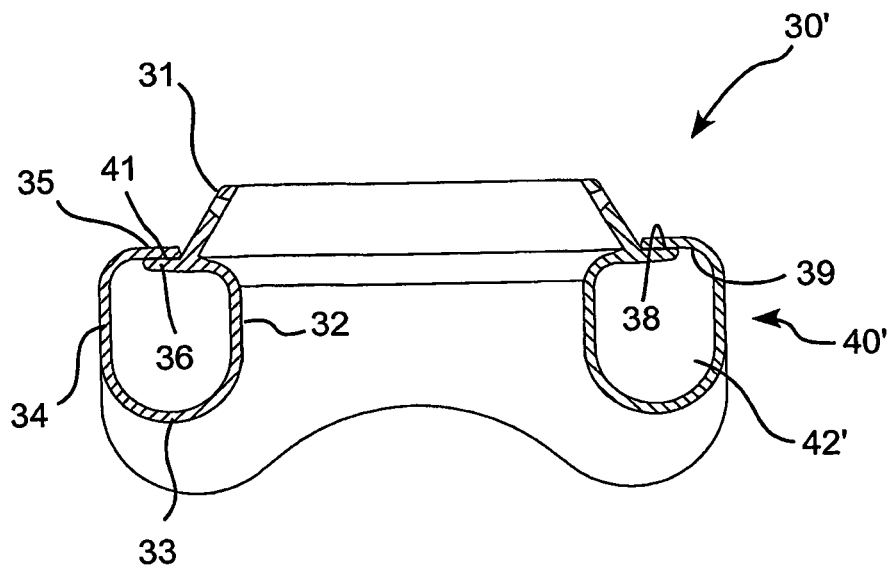
FIG. 9 shows the inflatable face seal shown in FIG. 8 after gluing.

FIGS. 8 and 9 show a second embodiment 30 of an inflatable face seal according to the invention. The second embodiment 30 comprises an attachment sleeve 31 for attachment to a rigid mask piece (not shown), an inner wall 32, a curved wall 33 which is in contact with the user's face when in use, an outer wall 34, a first flange 35 which is connected to the outer wall as a continuation of the outer wall and a second flange 36 which is connected to the inner wall as a continuation thereof. When it is desired to join the two flanges, an adhesive 37 such as glue is applied to the outwardly facing surface 38 of the second flange. The first flange 35 is then pulled upwards by stretching the walls of the seal such that the first flange 35 can be folded over the second flange 36. As in the first embodiment 1, due to the stretching and folding action, internal stresses result in the walls of the inflatable face seal which force the inwardly facing surface 39 of the first flange 35 against the outwardly facing surface 38 of the second flange. The final product 30' comprising an annular air-tight hollow portion 40' with a bonded joint 41 is shown in FIG. 9. The annular air-tight hollow portion 40' also defines an enclosed area 42'.

In this embodiment the bonded joint 41 is arranged on the outside of the attachment sleeve 31 instead of on the inside of the attachment sleeve 2 as was shown in the first embodiment 1. It should however be noted that the bonded joint could be located at any point along the periphery of the annular hollow volume.

It should also be noted that in the embodiments described, an adhesive such as glue was used to fasten the surfaces together. However, other forms of fastening, for example solvent bonding, could also be used.

It should also be mentioned that the final product could, after assembly, be heat treated in order to reduce the internal stresses in the final product. The two flanges will however still have been held together by internal stresses while the adhesive cured.

The invention claimed is:

1. An inflatable face seal for a respiratory mask, said face seal comprising an annular and inflatable air-tight hollow portion where a cross section through one section of the annular hollow portion includes a bonded joint which joins two overlapping flanges said two flanges being bonded together such that an inwardly facing surface of a first flange of the two overlapping flanges is in contact with an outwardly facing surface of a second flange of the two overlapping flanges wherein internal stresses in the inflatable face seal force the inwardly facing surface of the first flange towards the outwardly facing surface of the second flange.

2. The inflatable face seal according to claim 1, wherein the cross section includes an enclosed area and the bonded joint is located on a periphery of said enclosed area.

3. The inflatable face seal according to claim 1 or 2, wherein the two flanges are parallel to each other.

4. The inflatable face seal according to claim 1, wherein the second flange is formed as a flange which protrudes from an outer wall of the inflatable face seal and the first flange is formed as a hook attached to an inner wall of the inflatable face seal.

5. The inflatable face seal according to claim 1, wherein the first flange extends along the periphery of the cross section of the annular hollow portion in an opposite direction as the second flange.

6. A method of manufacturing an inflatable face seal for a respiratory mask, said method comprising the steps:
    molding an inflatable face seal having an annular hollow portion where a cross section through one portion of the annular hollow portion has a first flange and a second flange which are overlapping and radially spaced apart such that the first flange is arranged underneath the second flange in the radial direction,
    applying an adhesive to an outer surface of the second flange, and
    stretching a portion of said cross section located between the first flange and the second flange in order to fold the first flange over the second flange, such that an inner surface of the first flange is in contact with said outer surface of the second flange and such that the first flange is forced against the second flange via the internal stresses in the molded part due to the stretching.

7. The method of manufacturing an inflatable face seal according to claim 6, wherein the inflatable face seal is molded via an injection molding process in a closed mold.

8. An intermediate product in a manufacturing process of an inflatable face seal for a respiratory mask, said intermediate product comprising an annular hollow portion and where a cross section taken through one portion of the annular hollow portion includes an open semi circular portion having a first flange and a second flange arranged at opposite ends of the open semi circular portion, the second flange overlapping the first flange and being arranged farther from the center of the open semi circular portion than the first flange and where the first flange extends in an opposite direction from the second flange, wherein when the first and second flanges are brought into contact with each other and bonded together an annular and inflatable air-tight hollow portion is formed.

9. The intermediate product according to claim 8, wherein the first flange and the second flange are arranged essentially parallel to each other.

* * * * *